United States Patent [19]

Bodmer et al.

[11] 4,283,200
[45] Aug. 11, 1981

[54] METHOD AND APPARATUS FOR DETECTING CORROSION IN STEAM TURBINE INSTALLATIONS

[75] Inventors: Maurice A. Bodmer, Nussbaumen; Robert Svoboda, Wettingen, both of Switzerland

[73] Assignee: BBC Brown, Boveri & Co. Ltd., Baden, Switzerland

[21] Appl. No.: 90,250

[22] Filed: Nov. 1, 1979

[30] Foreign Application Priority Data

Nov. 9, 1978 [CH] Switzerland ............... 115241/78

[51] Int. Cl.³ .......................................... G01N 17/00
[52] U.S. Cl. ............................ 23/230 C; 422/53; 422/62
[58] Field of Search ............... 23/230 C; 422/9, 11, 422/53, 3, 119; 203/7

[56] References Cited

U.S. PATENT DOCUMENTS

| 2,976,123 | 3/1961 | Marsh et al. | 23/230 C X |
| 3,649,167 | 3/1972 | Sawyer | 422/11 X |

Primary Examiner—Barry Richman
Attorney, Agent, or Firm—Burns, Doane, Swecker & Mathis

[57] ABSTRACT

A process and a device for detecting the occurrence of corrosion during the operation of steam turbines are disclosed, wherein working medium is taken from the steam turbine and partially condensed. The condensate is separated from the remaining steam and the quantities of both the remaining steam and the condensate are determined. The condensate is continuously examined for aggressive materials. The condensate is then subjected to chemical and physical analysis in a test apparatus. To detect corrosivity, a prestressed metal test piece and a metal bursting disc are arranged in a condensate vessel in contact with the condensate.

17 Claims, 1 Drawing Figure

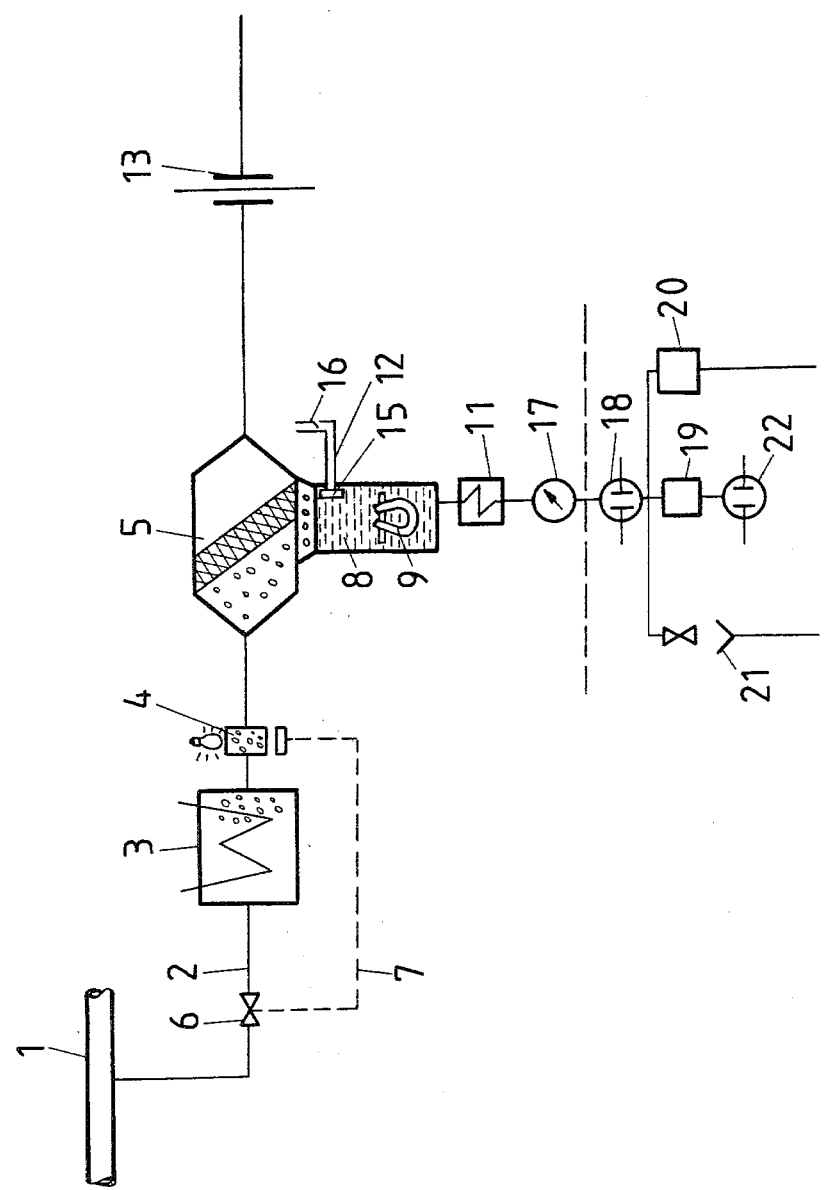

METHOD AND APPARATUS FOR DETECTING CORROSION IN STEAM TURBINE INSTALLATIONS

BACKGROUND AND SUMMARY OF THE PRESENT INVENTION

The present invention relates to a process for detecting the occurrence of corrosion in steam turbine installations during the operation of the latter, and to a device for carrying out the process.

When operating steam power stations supplied with steam generated from fossil or nuclear fuel, optimum availability of the installation is desired, coupled with the lowest possible fuel consumption. The aggressive impurities present in the steam, which are separated out with the first condensate, can cause corrosion in the circulation system and hence lead to material damage in the turbine and to detrimental oxide deposits in the heat exchangers. In addition to this corrosive damage, chemical destruction also occurs on materials which are mechanically stressed; for example, stress corrosion cracking, fatigue corrosion, vibration corrosion at the like.

Since the impurities responsible for damage of this type and chemical substances contained in the steam are present only in very small amounts and concentrations, a direct detection of such substances is possible only at great cost even if the most modern analytical techniques are used. Even the fitting of corrosion test pieces in the turbine does not give the desired result since the zone in which the first condensate is formed is very narrow and its exact position depends on various factors, such as load, cooling water temperature and the like. Moreover, observation of corrosion test pieces of this type during operation of the installation is possible only by using expensive apparatus.

It is, therefore, an object of the present invention to develop a process which detects corrosion in the installation during the operation of the latter, and to provide a device with which a measurement of the aggressivity of the working medium can be carried out continuously.

According to the present invention, the object stated above, and others, are achieved by the following process steps:

(a) working medium in the superheated state is taken from the steam circulation and partially condensed by cooling, (b) the condensate is separated from the remaining steam, after which the quantity of condensate and the quantity of remaining steam are determined, (c) the remaining steam is returned as steam or, after complete condensation, as water into the circulation, and (d) the condensate is continuously examined for its corrosivity or agressivity.

Advantageously, the working medium is measured optically for the purpose of quantitative control of the condensation step; at most, 2% of the working medium should be condensed.

The working medium is sampled directly from the steam circulation and only a small part, namely, at most, 2%, but preferably less than 1%, is condensed. The aggressive impurities are present in this condensate in a correspondingly concentrated form, and their aggressivity can be monitored continuously.

According to an advantageous process step, a metal test piece is exposed to the condensate in order to detect aggressivity. Since the condensate which is to be examined contains all the impurities present in the working medium in a concentrated form, the aggressivity and the corrosive action of the impurities can be detected earlier on these metal test pieces, around which the condensate flows, than the aggressivity and corrosive action of the impurities can be detected on metal parts of the turbine installation under attack.

According to another advantageous process step, the condensate is further cooled to a suitable temperature and subjected to chemical and physical analysis.

Cooling the condensate and passing it through various measuring cells permits the determination of different parameters to be measured parallel to one another. This procedure makes it possible to continuously recognize impurities which represent a potential risk to the materials in the thermal circulation, with sufficient time to take remedial measures.

The measuring device for carrying out the process according to the present invention essentially comprises a condenser, a water separator, two flow meters and a test apparatus, all of which can be connected to a steam sampling point on the installation.

The condenser cools the steam and hence forms a first condensate which is separated from the remaining steam in a water separator. The condensate is then passed to a test apparatus where, corresponding to the requirements, aggressivity tests on the noxious materials contained in the condensate and/or further chemical and physical analyses can be carried out.

BRIEF DESCRIPTION OF THE DRAWING

The single FIGURE is a simplified schematic representation of a preferred embodiment of the device for carrying out the process according to the present invention.

DETAILED DESCRIPTION OF THE PREFERRED EMBODIMENT

With reference to the single FIGURE, the superheated working medium from the steam circulation of a turbine is sampled at a point 1, via a line 2. The working medium passes into a condenser or cooler 3, where it is partially condensed by cooling. The condensation step is controlled quantitatively by a device 4 for measuring scattered light. The signal from the device 4 regulates the cross-section of the opening of a control element 6. The cooler 3 must be of such dimensions that it is possible to condense only a small part of the working medium taken from the steam circulation; namely, at most 2%, but preferably less than 1%.

In a water separator 5, the condensate is separated from the remaining steam and the latter is returned to the steam circulation via a flow meter; for example, an orifice plate 13. The condensate passes from the water separator 5 into a condensate vessel 8, where the condensate flows around a metal test piece 9 in order to detect aggressivity.

The metal test piece 9 is preferably prestressed and consists of the same material as the turbine materials. The prestressing of the metal test piece has the purpose of simulating the loading of the material in the turbine. During operation, this metal test piece 9 can be continuously observed; for example, through a sight glass (not shown) in a wall of the condensate vessel.

Of course, it is also possible to adjust the temperature of the condensate to the temperature of the condensate which is first obtained in the turbines as the result of the steam expansion. In this way, stressing of the metal test pieces can be effected under the conditions prevailing in the turbine.

Another possibility for examining corrosivity of the condensate, which can be used either in place of, or simultaneously with, the metal test piece 9 just described, is to provide a branch 12 in the wall of the condensate vessel 8. The branch 12 is then closed off from the atmosphere by a metal test piece in the form of a bursting disc 15. The material of the bursting disc 15 can be the same as the most highly stressed material in the turbine, but it is necessary to design the bursting disc 15 in such a way that it corrodes through more rapidly than the turbine components consisting of the same material. Towards the atmosphere, preferably an acoustic alarm instrument 16 is provided on the branch 12. The alarm instrument emits a signal when the bursting disc 14 corrodes through as a result of the excess pressure prevailing in the condensate vessel 8. It is also possible to use optical or electronic alarm instruments instead of an acoustic alarm instrument.

If a direct measurement to detect the aggressivity of a first condensate is desired in place of, or in addition to, the "indirect" process described above, the condensate may be cooled in a cooler 11 to a suitable temperature, preferably a temperature between 25° and 40° C. After flowing through a flow meter 17, the gross conductivity of the cooled condensate is measured in a conductivity meter 18.

If further chemical and physical analyses are necessary, these are carried out in instruments which preferably are arranged in parallel and can be switched off; for example, a conductivity meter 22 for determining the acid conductivity, cation exchanger 19, and a pH meter 20 for determining the pH value. To determine the content of Na, Cl and NH3 ions, appropriate measuring cells 21 can be provided.

The combination of different measuring instruments makes it possible to measure all the parameters of noxious materials present in the condensate continuously during the operation of the steam power installation.

In place of the embodiment described, the steam issuing from the water separator can also be condensed completely before it is returned into the circulation system. In this case, it is advantageous to measure the quantity of water instead of the described quantity of steam.

It is also to be understood that the entire measuring device can be designed as a solidly assembled mobile structure.

The principles and preferred embodiment of the present invention have been described in the foregoing specification. However, the invention which is intended to be protected is not to be construed as limited to the particular embodiment disclosed. The embodiment is to be regarded as illustrative rather than restrictive. Variations and changes may be made by those skilled in the art without departing from the spirit of the present invention.

What is claimed is:

1. A method of detecting the occurrence of corrosion in a steam turbine during operation, comprising the steps of:
    continuously withdrawing a representative sample of working steam from the turbine;
    condensing a portion of the working steam sample to form a condensate;
    controlling the quantity of said working steam sample which is condensed such that a predetermined percentage of the sample is condensed;
    separating the condensate from the remaining steam;
    determining the quantity of the remaining steam;
    continuously testing the condensate for corrosivity; and
    returning the remaining steam to the turbine.

2. The method of claim 1, wherein the quantity of the working steam sample which is condensed is controlled by taking a scattered light measurement of the working steam sample such that less than two percent of the working steam sample is condensed.

3. The method of claim 1, wherein the step of continuously testing includes exposing a metal test piece to the condensate to detect corrosivity.

4. The method of claim 1, further comprising the steps of:
    cooling the condensate; and subjecting the cooled condensate to chemical and physical analysis.

5. The method of claim 4, wherein a conductivity of the cooled condensate is measured.

6. The method of claim 4, wherein
    an acid conductivity of the cooled condensate is selectively measured;
    a pH value of the cooled condensate is selectively measured;
    a content of Na, Cl, and NH3 ions of the cooled condensate is selectively measured; and
    the step of continuously testing includes the step of continuously exposing a bursting disc to the condensate to detect corrosivity.

7. An apparatus for detecting corrosion in a steam turbine during operation comprising:
    first line means for continuously withdrawing a representative sample of working steam from the steam turbine at a predetermined point in the steam turbine;
    condenser means for condensing a portion of the steam sample received through the first line means to form a condensate;
    separator means for separating the condensate from the remaining steam;
    testing means for continuously testing the condensate for corrosivity;
    second line means for returning the remaining steam to the turbine;
    a flow meter for determining the quantity of remaining steam arranged in the second line means; and
    control means for controlling the quantity of said working steam sample which is condensed such that a predetermined percentage of the sample is condensed.

8. The apparatus of claim 7, wherein the control means comprises a device for measuring scattered light after the working steam sample has been passed through the condenser means, said device controlling the opening cross-section of a control element disposed upstream from the condenser means.

9. The apparatus of claim 7 or 8 wherein less than two percent of the working steam is condensed.

10. The apparatus of claim 7, further comprising:
    cooling means for cooling the condensate; and
    analysis means for analyzing the cooled condensate, the analysis means being arranged downstream from the cooling means.

11. The apparatus of claim 10, wherein the analysis means includes a conductivity meter.

12. The apparatus of claim 10, wherein the analysis means includes:
a plurality of instruments arranged in parallel, said instruments being selectively operable for measuring physical and chemical properties of the cooled condensate and including an acid conductivity meter, a pH meter, and Na, Cl, and $NH_3$ ion detectors.

13. The apparatus of claim 10, further comprising a flow meter arranged downstream from the cooling means and upstream from the analysis means.

14. The apparatus of claim 7, wherein the testing means comprises a metal test piece arranged in a condensate vessel in constant contact with the condensate.

15. The apparatus of claim 14, wherein the metal test piece is prestressed and is of the same material as turbine parts subject to corrosion.

16. The apparatus of claim 14, wherein the testing means further comprises a metal bursting disc provided in a wall of the condensate vessel, a side of the bursting disc being in continuous contact with the condensate.

17. The apparatus of claim 16, further comprising alarm means for indicating a bursting of the bursting disc.

* * * * *

UNITED STATES PATENT AND TRADEMARK OFFICE
CERTIFICATE OF CORRECTION

PATENT NO. : 4,283,200
DATED : August 11, 1981
INVENTOR(S) : Maurice A. Bodmer, Robert Svoboda It is certified that error appears in the above—identified patent and that said Letters Patent is hereby corrected as shown below:

On the first page, under "Foreign Application Priority Data", after "Nov. 9, 1978 [CH] Switzerland......" delete "115241/78" and insert therefor --11524/78--.

Signed and Sealed this

Third Day of November 1981

[SEAL]

Attest:

Attesting Officer

GERALD J. MOSSINGHOFF

Commissioner of Patents and Trademarks